(12) United States Patent
Dishon

(10) Patent No.: US 9,999,486 B2
(45) Date of Patent: Jun. 19, 2018

(54) SPRING MECHANISM FOR POWER DEVICE

(71) Applicant: Ranir, LLC, Grand Rapids, MI (US)

(72) Inventor: Bryan J. Dishon, Alto, MI (US)

(73) Assignee: Ranir, LLC, Grand Rapids, MI (US)

( * ) Notice: Subject to any disclaimer, the term of this patent is extended or adjusted under 35 U.S.C. 154(b) by 457 days.

(21) Appl. No.: 14/661,680

(22) Filed: Mar. 18, 2015

(65) Prior Publication Data

US 2016/0276913 A1    Sep. 22, 2016

(51) Int. Cl.
| | |
|---|---|
| *H02K 33/02* | (2006.01) |
| *A61C 17/34* | (2006.01) |
| *A61C 17/22* | (2006.01) |
| *H02K 33/16* | (2006.01) |

(52) U.S. Cl.
CPC ............ *A61C 17/34* (2013.01); *A61C 17/221* (2013.01); *A61C 17/3418* (2013.01); *H02K 33/02* (2013.01); *H02K 33/16* (2013.01)

(58) Field of Classification Search
CPC ..................... H02K 33/00–33/18; A61C 17/34
USPC ................ 310/15–39, 47, 50; 15/22.1, 22.12
See application file for complete search history.

(56) References Cited

U.S. PATENT DOCUMENTS

| | | |
|---|---|---|
| 2,759,114 A | 8/1956 | Wendel et al. |
| 3,335,443 A | 8/1967 | Parisi |
| 3,375,820 A | 4/1968 | Kuris |
| 3,488,788 A | 1/1970 | Robinson |
| 3,535,726 A | 10/1970 | Sawyer |
| 3,676,218 A | 7/1972 | Sawyer |
| 3,828,770 A | 8/1974 | Kuris |
| 3,980,906 A | 9/1976 | Kuris |
| 4,192,035 A | 3/1980 | Kuris |
| 4,333,197 A | 6/1982 | Kuris |

(Continued)

FOREIGN PATENT DOCUMENTS

| | | | |
|---|---|---|---|
| CN | 102111032 | 6/2011 | |
| CN | 102111032 A | * 6/2011 | ............. H02K 33/00 |

(Continued)

OTHER PUBLICATIONS

Machine Translation, Wang, CN 102111032 A, Jun. 2011.*

(Continued)

*Primary Examiner* — Thomas Truong
(74) *Attorney, Agent, or Firm* — Warner Norcross + Judd LLP (57) ABSTRACT

A spring mechanism for an electromagnetic drive unit converts or translates the movement and/or actuation of the electromagnet into a desired movement of the workpiece and enables simple and efficient tuning of the workpiece movement. The spring mechanism includes a housing, a spring connected to the housing, wherein at least a section of the spring is movable with respect to the housing, a drive shaft that includes a first end having a magnet and a second end for attachment to a workpiece, and an adjustable tuning element connecting the drive shaft to the movable portion of the spring. In one embodiment, the spring may be a flat spring, and the movable section may be a positioned between a pair of cutouts defined in the spring. In one embodiment, the adjustable tuning element is connected to the spring such that the adjustable tuning element places the movable portion of the spring under a degree of tension.

18 Claims, 8 Drawing Sheets

(56) References Cited

U.S. PATENT DOCUMENTS

| | | | |
|---|---|---|---|
| 4,991,249 A | 2/1991 | Suroff | |
| 5,138,733 A | 8/1992 | Bock | |
| 5,150,492 A | 9/1992 | Suroff | |
| 5,158,279 A | 10/1992 | Laffey et al. | |
| 5,189,751 A * | 3/1993 | Giuliani | A61C 17/20 15/22.1 |
| 5,247,716 A | 9/1993 | Bock | |
| 5,311,632 A | 5/1994 | Center | |
| 5,369,831 A | 12/1994 | Bock | |
| 5,378,153 A | 1/1995 | Giuliani et al. | |
| 5,469,291 A | 11/1995 | Plesko | |
| 5,546,624 A | 8/1996 | Bock | |
| 5,613,259 A | 3/1997 | Craft et al. | |
| 5,784,742 A | 7/1998 | Giuliani et al. | |
| 6,845,537 B2 | 1/2005 | Wong | |
| 6,918,300 B2 | 7/2005 | Grez et al. | |
| 7,024,717 B2 | 4/2006 | Hilscher | |
| 7,067,945 B2 | 6/2006 | Grez et al. | |
| 7,086,111 B2 | 8/2006 | Hilscher | |
| 7,207,080 B2 | 4/2007 | Hilscher | |
| 8,336,155 B2 | 12/2012 | Crossman et al. | |
| 2002/0092104 A1 | 7/2002 | Ferber et al. | |
| 2004/0255409 A1 | 12/2004 | Hilscher | |
| 2005/0000044 A1 | 1/2005 | Hilscher | |
| 2005/0011025 A1 | 1/2005 | Hilscher | |
| 2006/0168745 A1* | 8/2006 | Kobayashi | A61C 17/3445 15/22.1 |
| 2007/0234493 A1 | 10/2007 | Hilscher | |
| 2008/0010771 A1 | 1/2008 | Hilscher | |
| 2008/0020351 A1 | 1/2008 | Hilscher | |
| 2008/0020352 A1 | 1/2008 | Hilscher | |
| 2008/0022469 A1 | 1/2008 | Hilscher | |
| 2008/0022470 A1 | 1/2008 | Hilscher | |
| 2008/0022471 A1 | 1/2008 | Hilscher | |
| 2008/0022501 A1 | 1/2008 | Hilscher | |
| 2008/0022503 A1 | 1/2008 | Hilscher | |
| 2008/0028549 A1 | 2/2008 | Hilscher | |
| 2008/0032265 A1 | 2/2008 | Hilscher | |
| 2008/0034515 A1 | 2/2008 | Hilscher | |
| 2008/0185922 A1* | 8/2008 | Kressner | A61C 17/225 310/36 |

FOREIGN PATENT DOCUMENTS

| | | |
|---|---|---|
| DE | 20321197 | 6/2006 |
| DE | 20321198 | 10/2006 |
| EP | 0802614 | 10/1997 |
| EP | 0576620 | 9/1998 |
| EP | 0893106 | 1/1999 |
| EP | 0695131 | 3/2000 |
| EP | 0625017 | 5/2000 |
| EP | 0781105 | 11/2004 |
| EP | 1684401 | 7/2006 |
| JP | 2005180375 | 7/2005 |
| JP | 2009-240155 | 10/2009 |
| WO | 9401054 | 1/1994 |
| WO | 03092534 | 11/2003 |
| WO | 03092535 | 11/2003 |
| WO | 2004000156 | 12/2003 |
| WO | 2004054467 | 7/2004 |
| WO | 2005000149 | 1/2005 |
| WO | 2005058189 | 6/2005 |
| WO | 2005058190 | 6/2005 |
| WO | 2006067758 | 6/2006 |
| WO | 2007029201 | 3/2007 |
| WO | 2007122491 | 11/2007 |
| WO | 2008001302 | 1/2008 |
| WO | 2014103225 | 7/2014 |

OTHER PUBLICATIONS

Partial European Search Report for Application No. 15165695.6, dated Aug. 24, 2016.
EP16158271.3 Partial European Search Report dated Jul. 22, 2016.

* cited by examiner

SPRING MECHANISM FOR POWER DEVICE

BACKGROUND OF THE INVENTION

The present invention is directed to electromagnetically powered devices, and, more particularly, to powered devices such as electric toothbrushes having an electromagnetic drive unit.

One method for actuating the bristles, or other cleaning elements, of an electric toothbrush or another device having a powered handle is an electromagnetic drive positioned within the handle portion of the toothbrush or other device. The electromagnet can be actuated by a switch to alternate polarity at a desired frequency. A movable permanent magnet (or a pair of permanent magnets) is positioned proximate to the electromagnet, such that the permanent magnet is driven to oscillate at an oscillating frequency by the electromagnet when the electromagnet is actuated. A neck, which may or may not be elongated, including a workpiece such as a brush head is typically attached to the permanent magnet, such that the workpiece is driven to oscillate by the movement of the permanent magnet.

Recognizing the need to replace certain aspects of these workpieces, such as toothbrush bristles, after they are worn out or in order to provide more options, e.g., to attach a different head with a different function, manufacturers have designed replacement heads that fit onto separate electromagnetic drive units. The drive units may include the power source, switch, fixed electromagnet, movable permanent magnet and drive shaft, with the replacement heads including a neck and a workpiece such as a toothbrush head. In some instances, the replacement heads may further include the permanent magnet, drive shaft and workpiece. The replacement heads can be removably attached to the drive units, for instance, by threading or otherwise connecting a portion of the replacement head onto a portion of the drive unit.

More recently, manufacturers have attempted to control the movement of these workpieces, in order to provide a more efficient and desirable workpiece motion. For example, in the case of electric toothbrushes, manufacturers have attempted to control the movement of the cleaning elements in a rotational motion about the central longitudinal axis of the toothbrush. Difficulties arise in doing so, especially in the case of toothbrushes with electromagnetic drives, because the generally linear oscillation caused by the electromagnet must be converted into the desired rotational motion. Some replacement heads include parts that may contribute to vibrations and/or noise in the electric toothbrush that may be undesirable or annoying. In each situation, the motion of the workpiece can vary dramatically as the frequency of the electromagnet approaches the resonant frequency of the drive shaft and workpiece.

SUMMARY OF THE INVENTION

The present invention provides a spring mechanism for an electromagnetically powered device that converts or translates the movement and/or actuation of the electromagnet into a desired movement of the workpiece and enables simple and efficient tuning of the workpiece movement.

In one embodiment, the spring mechanism includes a housing, a spring connected to the housing, wherein at least a portion of the spring is movable with respect to the housing, a drive shaft that includes a first end having a magnet and a second end for attachment to a workpiece, and an adjustable tuning element connecting the drive shaft to the movable portion of the spring.

In one embodiment, the spring may be a flat spring, and the movable portion of the spring may be a spring section positioned between a pair of cutouts defined in the spring. The size and shape of the cutouts may also be varied in order to control the workpiece movement.

In one embodiment, the adjustable tuning element extends from the drive shaft to the movable portion of the spring, and is connected to the spring such that the adjustable tuning element places the movable portion of the spring under a degree of tension. The adjustable tuning element may be threadedly connected between the drive shaft and the movable portion of the spring, such that the threaded connection enables adjustment of the amount of the tension on the movable portion of the spring. More particularly, the tuning element may be a bolt extending through the movable portion of the spring, through the drive shaft, and into a nut on an opposite surface of the drive shaft.

The drive shaft may be rotatable about a pair of bearing surfaces defining an axis of rotation extending along the bearing surfaces, and the adjustable tuning element may be positioned between the bearing surfaces. The bearing surfaces may be formed by a pair of rockers extending from the drive shaft.

The spring mechanism may be implemented into a toothbrush drive unit or some other personal care device drive unit, wherein the bristle head and neck are capable of being removed from the drive unit and replaced. In another embodiment, however, the spring mechanism may be incorporated into a replacement head for a toothbrush or for some other personal care device, wherein the bristle head and neck, drive shaft, and spring are replaceable.

The present invention also provides a method for manufacturing a spring mechanism for an electric toothbrush or other personal care device, including the steps of: providing a fixed housing defining a generally hollow interior; providing a drive shaft extending at least in part into the hollow interior of the fixed housing, the drive shaft having a first end and a second end, the first end including a magnet and the second end adapted to receive a workpiece; connecting a spring member to the fixed housing, the spring member having a movable section; connecting the spring member to the drive shaft with an adjustable tuning member; and adjusting the tuning member to provide a desired degree of tension on the movable section of the spring.

DETAILED DESCRIPTION OF THE CURRENT EMBODIMENTS

I. Overview

A spring mechanism for use in powered devices such as an electric toothbrush is shown in FIGS. 1-19 and generally designated 10. The spring mechanism 10 includes: a fixed element 11 connected to a drive unit housing 12, a spring 14 connected to the fixed element 11, wherein at least a portion 16 of the spring 14 is movable with respect to the fixed element 11 and the housing 12, a drive shaft 18 that includes a first end 20 having a magnet and a second end 24 for attachment to a workpiece 26, and an adjustable tuning element 28 connecting the drive shaft 18 to the movable section 16 of the spring 14.

In operation, the spring mechanism 10 operates to convert or translate movement of the magnet into a desired movement of the workpiece 26 at a desired frequency. The magnet is driven by a drive, such as an electromagnet 30, positioned adjacent to the magnet. The adjustable tuning element 28 enables simple adjustment of the workpiece movement and frequency. In the illustrated embodiment, the workpiece 26 is a replacement head for an electric toothbrush and the spring mechanism 10 provides the toothbrush head with a desired motion. In an alternative embodiment, the spring mechanism 10 may form part of the replacement head, rather than part of the drive unit housing.

II. Structure

Figure 1:
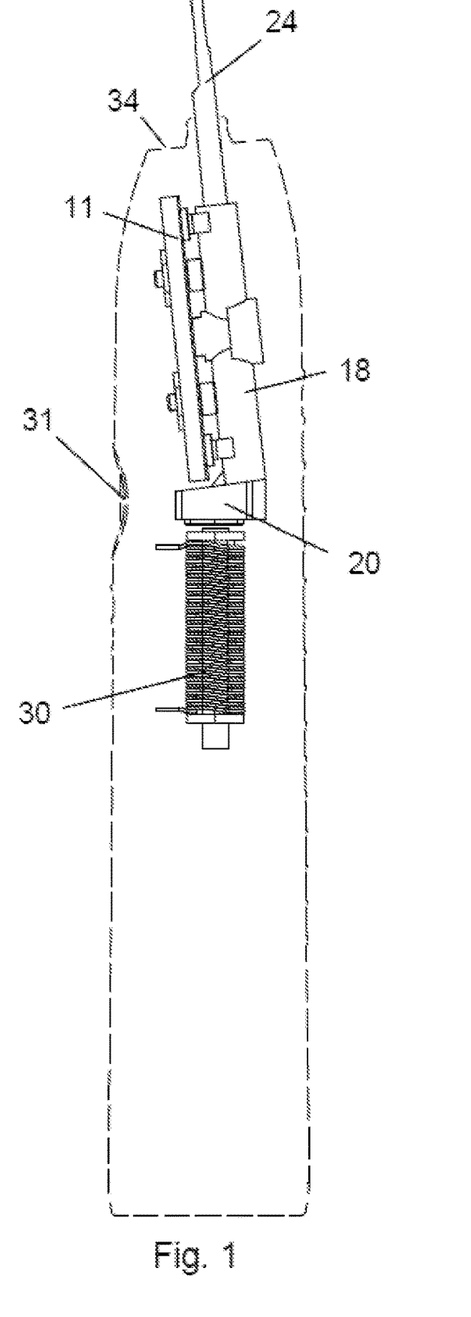
FIG. 1 is a side view according to one embodiment of the present invention showing a spring mechanism as disposed within a handle housing shown in broken lines, and including an electromagnet within the handle housing.
Figure 2:
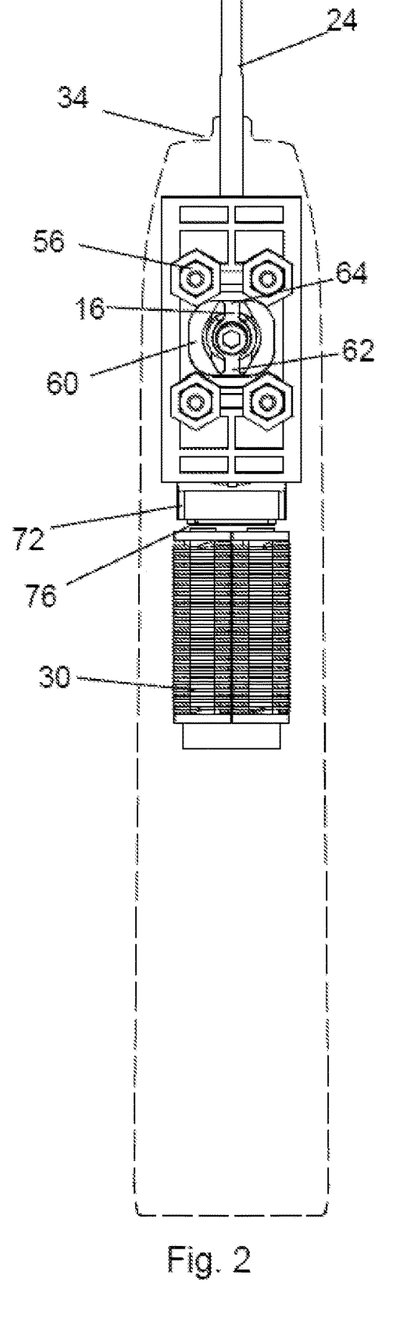
FIG. 2 is a front view thereof.
Figure 3:
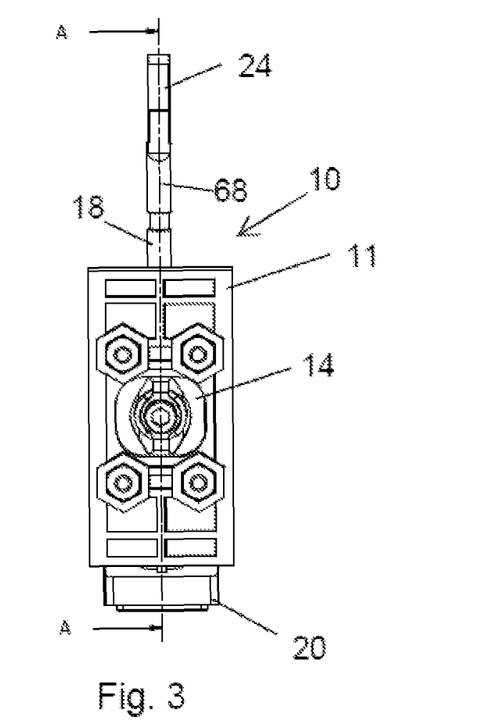
FIG. 3 is a front view of a spring mechanism for a power device according to one embodiment.
Figure 4:
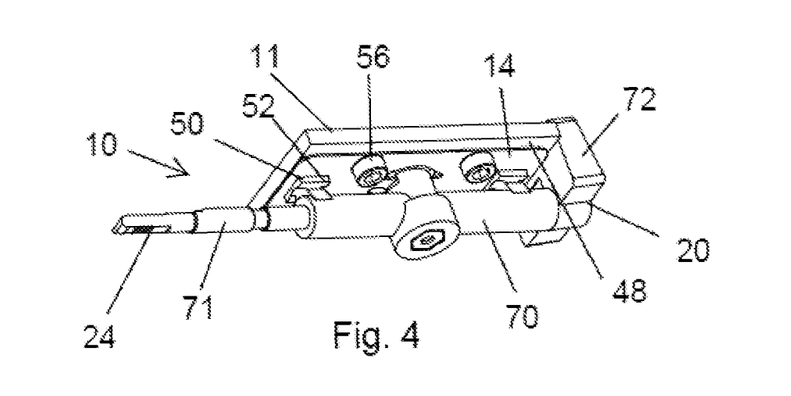
FIG. 4 is a rear perspective view thereof.
Figure 5:
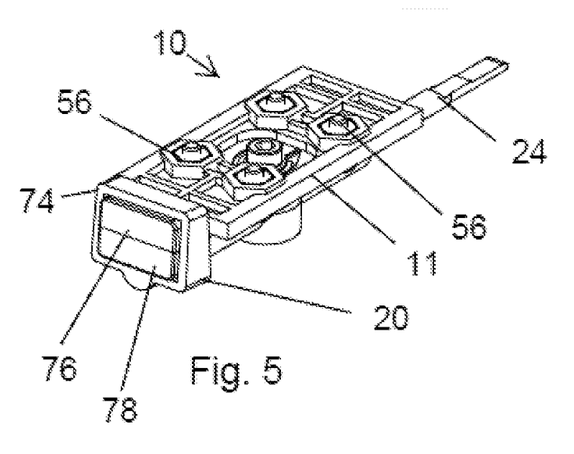
FIG. 5 is a front perspective view thereof.
Figure 20:
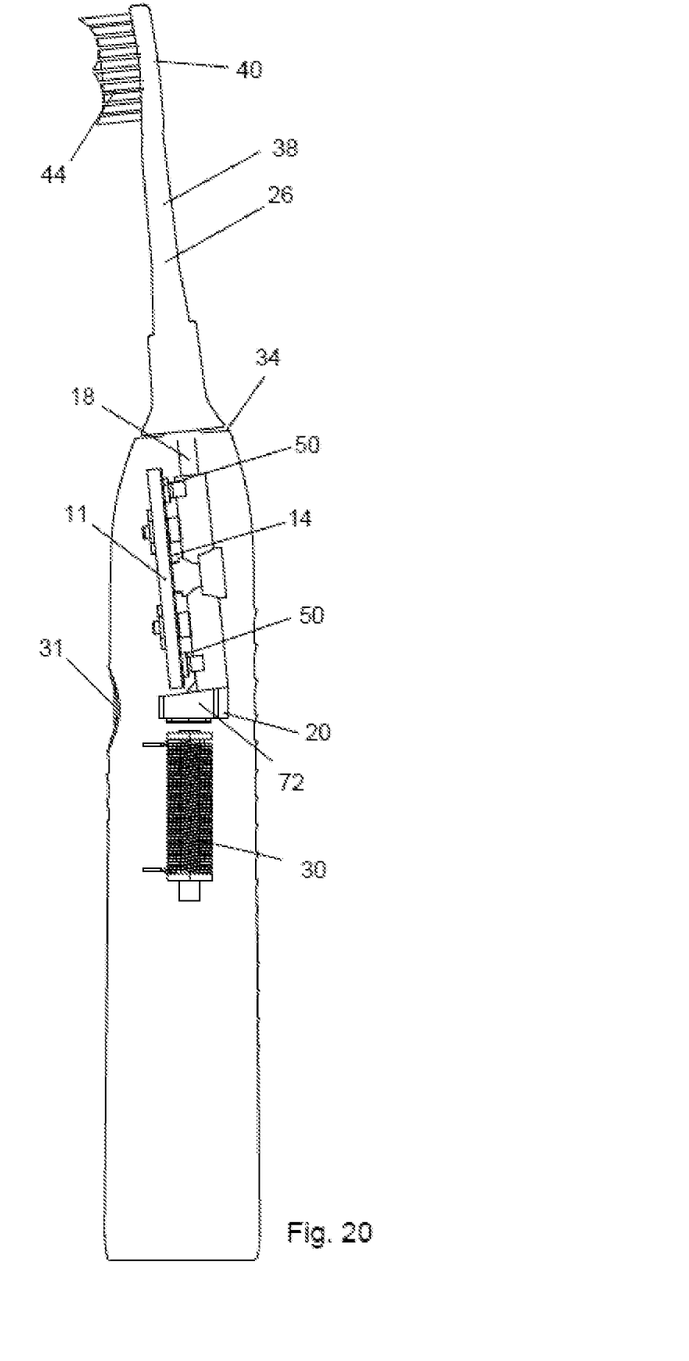
FIG. 20 is a side view of an electric toothbrush with a replacement head attached wherein the electromagnet and spring mechanism are visible through the drive unit housing.

As noted above, electromagnetic drive units are well known; therefore, the drive unit housing 12 and electromagnet 30 will not be described in great detail herein. Suffice it to say that the drive unit housing 12 generally forms a handle for the drive unit and includes a power source (not shown) within the housing, such as a battery or AC power supply, and a switch 31 that is operable by the user. The drive unit housing 12 includes a drive mechanism that may be a DC drive or an AC drive. In one embodiment, the drive unit housing 12 includes an electromagnet 30 positioned within the drive unit housing 12 that is actuated when the user presses the switch 31. The electromagnet 30, or a pair of electromagnets, may be actuated to oscillate between positive and negative polarities within the drive unit housing 12. The oscillation may be over a range of resonant frequencies of the electromagnet. As depicted in FIGS. 1, 2 and 20, the electromagnet 30 is centrally positioned within the drive unit housing 12 proximate the first end 20 of the spring mechanism 10 drive shaft 18, and the spring mechanism 10 is positioned within the housing 12. A portion of the drive shaft 18 including the second end 24 of the drive shaft 18 extends outwardly from an end 34 of the housing 12 for receiving the workpiece 26.

The spring mechanism 10 may be designed for removably attaching to the workpiece 26, such as a replacement toothbrush head or another type of device intended for rotational oscillation. Referring to FIGS. 10-20, in one embodiment, the workpiece 26 is a toothbrush head that generally includes elongated neck 38 with a head 40 at one end, and a receptacle (not shown) at the opposite end. The receptacle is sized to receive the second end 24 of the drive shaft 18. As illustrated, the head 40 includes a plurality of bristles 44 that may be of various lengths extending outwardly from the head 40. In another embodiment, the head 40 may include one or more alternative cleaning elements, such as elastomeric elements, extending from the head 40. In yet another embodiment, referenced above, the workpiece 26 may form a part of a larger replacement head that also includes the spring mechanism 10. In such an embodiment, the drive unit housing 12 may include structure, such as threads, for connecting to the replacement head and a portion of the spring mechanism 10 may extend into an opening in the drive unit housing 12 to enable the spring mechanism 10 to be driven by the electromagnet 30.

Referring to FIGS. 1-20, the spring mechanism 10 includes the fixed element 11, spring 14, drive shaft 18, and adjustable tuning element 28. In the illustrated embodiment, the fixed element 11 is connected to the larger drive unit housing 12 by conventional means. The fixed element 11 is connected to the drive unit housing 12 in such a way that the fixed element 11 is fixed in place with respect to the drive unit housing 12. In one embodiment, the fixed element 11 is a generally flat, molded plastic plate having an upper surface 46 and a lower surface 48. The fixed element 11 may otherwise be formed from a variety of different materials, and in one embodiment may be formed integrally with the drive unit housing 12. In the illustrated embodiment of FIGS. 1-7, the lower surface 48 includes a pair of spaced-apart protrusions or bosses 50 extending outwardly from the lower surface 48. The outer surfaces 52 of these bosses 50 may be concave in shape to form a portion of an engagement surface when engaged with a bearing member 80 on the drive shaft 18 described below. A second embodiment of the fixed element 11' is shown in FIGS. 10-19. In this variation (see FIG. 17), the fixed element 11' does not include outwardly extending bosses 50. Instead, a pair of concave depressions 50' in the lower surface 48' of fixed element 11' form engagement surfaces 52' that function similarly to the outer surfaces 52 on the bosses 50.

The spring member 14 is attached to the fixed element 11. In the illustrated embodiment, the spring member 14 is a generally flat plate formed of a resilient material such as spring steel. As illustrated, the spring 14 is attached to the fixed element 11 with four fasteners 56 that extend through the fixed element 11 and the spring 14. The fasteners 56 hold at least a portion of the spring 14 fixed with respect to the fixed element 11 and the drive unit housing 12. Of course, the spring 14 could be fixedly secured to the fixed housing 11 or the drive unit housing 12 in a variety of other conventional methods.

In one embodiment, the spring 14 further includes a movable section 16. As illustrated, the movable section 16 is a strip of the spring member 14 that is formed between a pair of symmetric cutouts 60 in the spring 14. In the illustrated embodiment, the movable section 16 is positioned centrally within the spring 14, however, the movable section 16 may otherwise be positioned at alternative locations on the spring as desired depending on the application. By virtue of the cutouts 60, the movable section 16 is formed to include a first end 62 and a second end 64 opposite the first end, such that the movable section 16 forms a torsion bar between the first 62 and second 64 ends that may twist back and forth along a spring axis defined along the longitudinal extent of the movable section 16 while the ends 62, 64 remain fixed. The size and shape of the cutouts 60 will control the degree of flexibility and torsional rotation of the movable section 16 about the spring axis. In the illustrated embodiment, each cutout 60 is generally semi-circular, with the convex surfaces facing away from the movable section 16; however, the shape of the cutouts 60 may be changed in order to alter the characteristics of the movable portion 16. In order to increase flexibility in the movable section 16, and thus increase the movement of the drive shaft 18 and workpiece 26, the cutouts may be made larger, and the movable section thinner. In one embodiment, the size and shape of the cutouts 60 and the movable section 16 are preselected by the manufacturer in accordance with the size and shape of the drive shaft 18 and workpiece 26 in order to produce a desired workpiece motion, for example, wherein the frequency of the electromagnetic drive mechanism 30 approximates the resonant frequency of the workpiece 26. In one embodiment, the movable section 16 defines a central opening 66 for receiving the adjustable tuning element 28 as described in more detail below. Other characteristics of the spring may also be altered to change the motion of the workpiece 26, for example, a thicker spring material will increase the force required to twist the spring and reduce the amount that the spring will twist during operation. Additional elements such as slots and holes may further be incorporated into the spring, or multiple springs, to provide the spring(s) with desired characteristics. In one embodiment, the spring 14 may include holes that enable the bosses 50 on the fixed element to extend through the spring 14 and into engagement with the drive shaft 18. Alternatively, the spring may be configured without these openings such that the spring forms engagement surfaces for the drive shaft 18.

Although the movable section 16 of the spring 14 is illustrated as a portion of the larger spring member that is defined between a pair of cutouts, it should be understood that in an alternative embodiment, the spring 14 may be comprised solely of a movable portion, such as a generally flat strip of spring material that is fixed on opposite ends to form a torsion bar with characteristics similar to that of the movable section 16.

The drive shaft 18 is a generally elongated member defining a longitudinal axis 68, and having a first end 20 and a second end 24 opposite the first end. The drive shaft 18 may be formed integrally as a single unitary piece of material, but in the illustrated embodiment is formed from two materials and two pieces including a molded plastic member 70 that includes the first end 20 of the drive shaft 18 and a metal member 71 that extends into a recess in the plastic member 70 along the longitudinal axis and includes the second end 24 of the drive shaft 18. As illustrated, the first end 20 of the drive shaft 18 includes a base 72, which is a generally flat plate extending outwardly from the first end 20 of the drive shaft 18 in a direction generally perpendicular to the longitudinal axis 68 of the drive shaft 18. The base 72 has a lower surface 74 that supports a pair of permanent magnets 76, 78 of opposite polarities for instance, by molding the magnets into the base 72, or with an adhesive or by other known means. Alternatively, the magnets 76, 78 may be indirectly connected to the base 72 by an intermediate plate, for example. As shown in FIGS. 1 and 2, when assembled, the magnets 76, 78 are positioned adjacent to the electromagnet 30. As a result of the magnets 76, 78 being positioned on the base 72 such that they are offset from the longitudinal axis of the drive shaft 18, the electromagnet will cause the magnets 76, 78 to move the base 72 in an arcuate path. As illustrated, the base 72 includes an outer periphery that is smaller than the size of the interior of the drive unit housing 12, so that the base 72 is capable of moving back and forth and/or up and down within the drive unit 12 housing. In one embodiment, the magnets 76, 78 may be replaced by a ferromagnetic material, such as steel, that can be attracted to and repelled by the electromagnet 30 within the drive unit housing 12.

Figure 15:
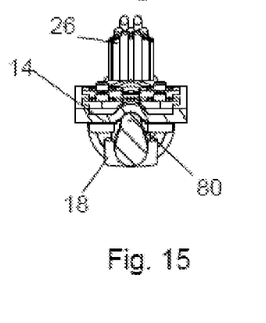
FIG. 15 is a cross sectional view thereof taken along line C-C in FIG. 14.
Figure 16:
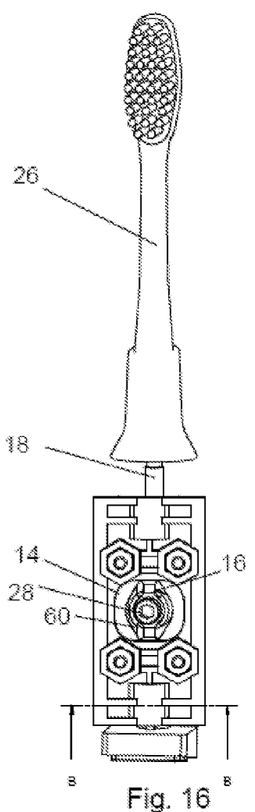
FIG. 16 is a front view of a spring mechanism with a workpiece connected thereto, with the drive shaft and spring in a left-rotated position.

The remainder of the plastic member 70 of the drive shaft 18 facilitates engagement between the outer surfaces 52, 52' on the fixed element 11 as well as the connection between the drive shaft 18 and the movable section 16 of the spring 14. Referring now to FIG. 15, the drive shaft 18 includes a pair of rounded protrusions 80 forming rounded bearing surfaces that engage the engagement surfaces 52, 52' on the fixed element 11 to determine a rocking-style relationship between the drive shaft 18 and the fixed element 11, wherein the rounded protrusions 80 can rock back and forth on the concaved engagement surfaces 52. In between the rounded protrusions 80, the drive shaft 18 includes structure for connecting the drive shaft 18 to the movable section of the spring 16. In one embodiment, the drive shaft 18 defines a fastener hole 82 extending therethrough for receiving the adjustable tuning element 28 as described in more detail below. In another embodiment, an alternative structure may be used to facilitate a rocking-style movement of the drive shaft 18 with respect to the fixed housing 11. For example, rounded protrusions may be included on the fixed housing 11 or spring member 14 to engage concave surfaces on the drive shaft 18, or the drive shaft 18 may be connected to the fixed housing with hinges. In each case, the connection of the drive shaft 18 to the fixed element 11 causes the drive shaft 18 to move in an arcuate motion upon actuation of the electromagnet, the electromagnet 30 causing the permanent magnets 76, 78 to move in an oscillating motion, and the connection of the drive shaft 18 to the fixed element 11 causing the drive shaft to move in an arcuate path about an axis that is parallel with the spring axis and the longitudinal axis 68 of the drive shaft 18 along an axis generally extending through the bearing surfaces.

Finally, the second end 24 of the drive shaft 18 is shaped to attach to the workpiece 26. In the illustrated embodiment, the second end 24 includes a shape that is formed to extend into the receptacle in the workpiece 26 and prevent rotation or axial displacement of the workpiece 26 with respect to the drive shaft 18. Referring now to FIGS. 1 and 2, the second end 24 extends outwardly beyond an end of the drive unit housing 12 for attachment to the work piece 26.

Figure 6:
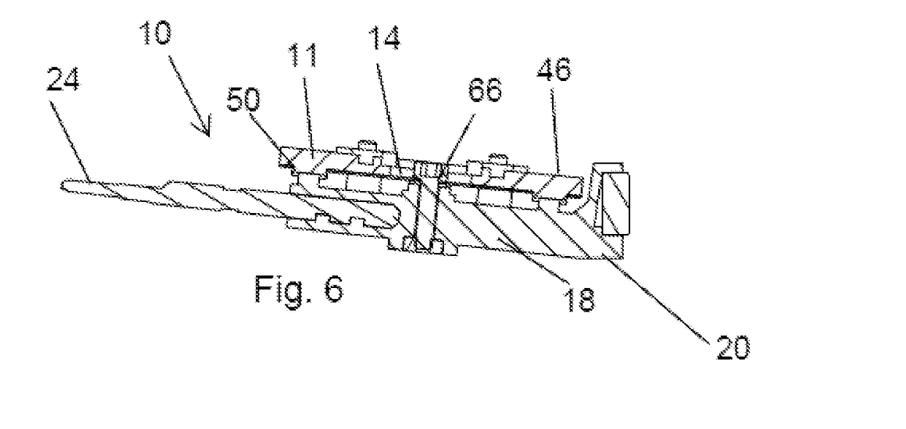
FIG. 6 is a side cross sectional view taken along line A-A in FIG. 3, showing the spring in a neutral position.
Figure 6A:
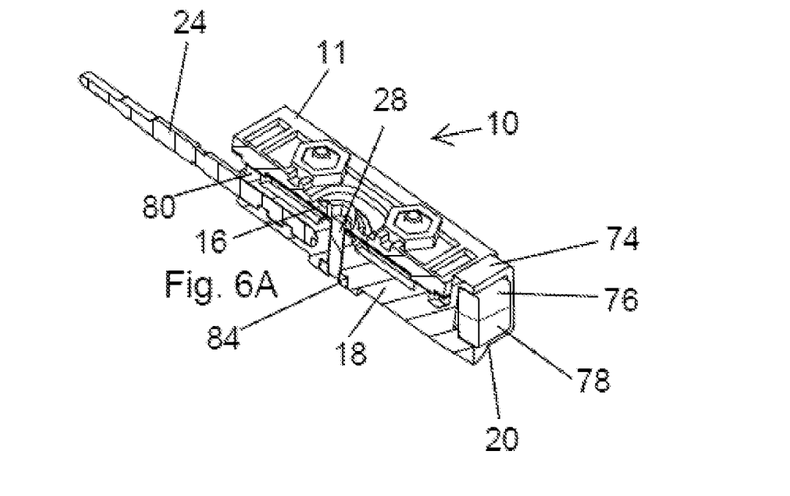
FIG. 6A is a perspective cross sectional view thereof.
Figure 7:
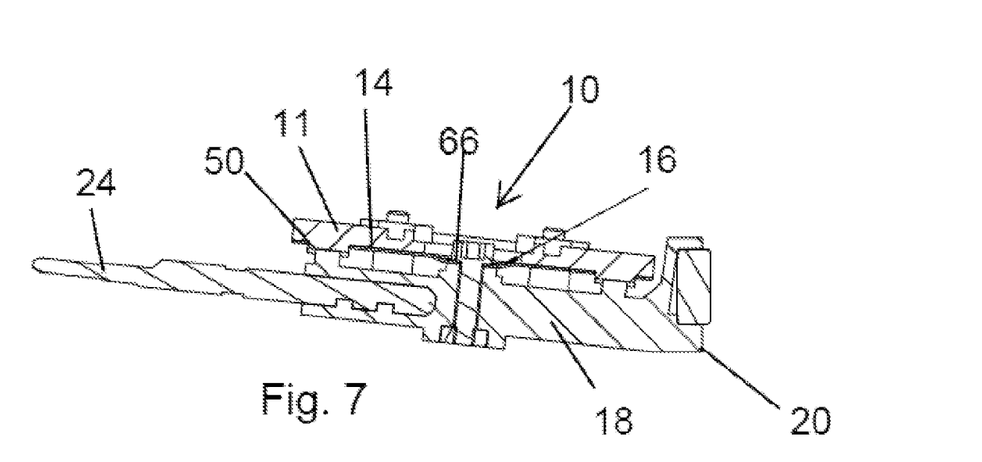
FIG. 7 is a side cross sectional view taken along line A-A in FIG. 3, showing the spring in a more tensioned positioned.
Figure 7A:
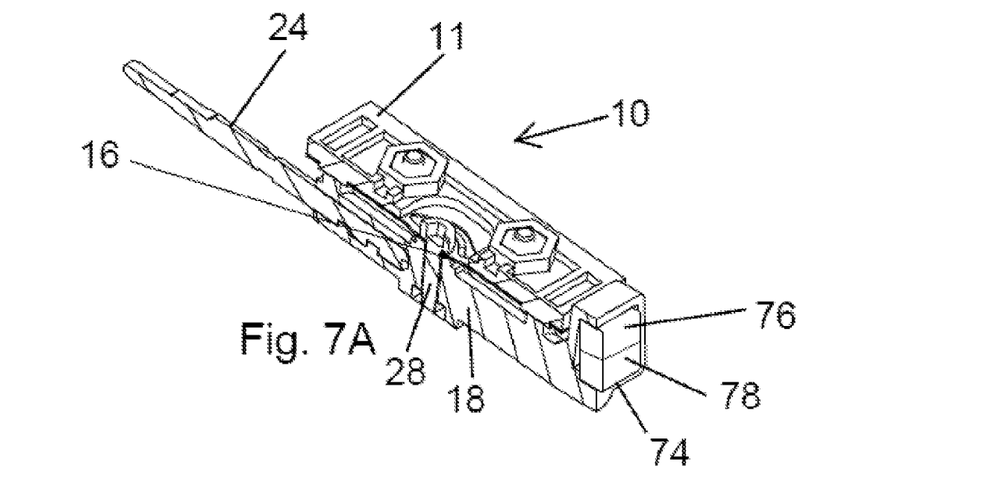
FIG. 7A is a perspective cross sectional view thereof.
Figures 8, 10, 12:
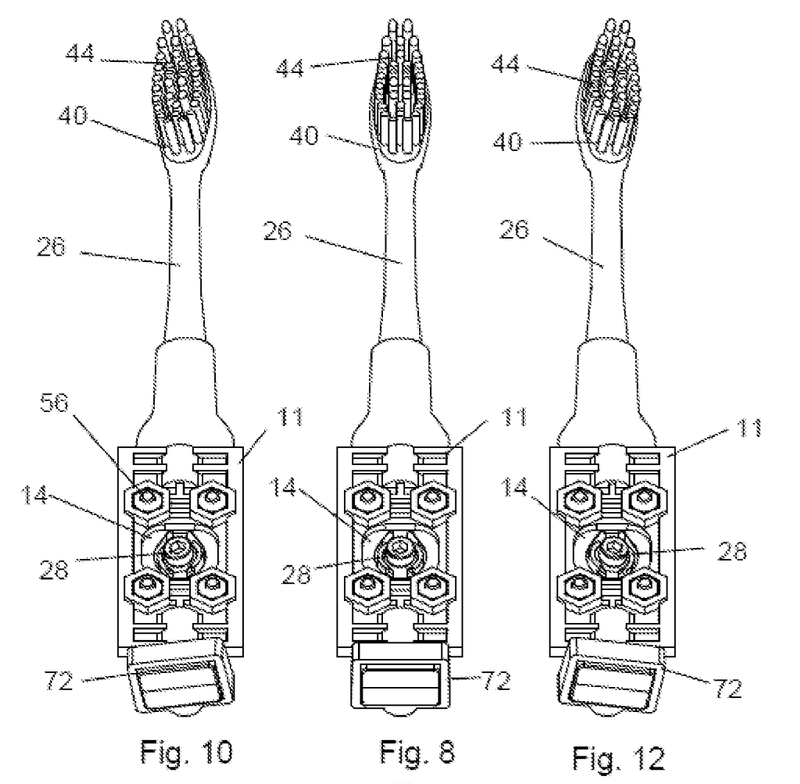
FIG. 8 is a perspective view of a spring mechanism with a workpiece connected thereto, with the drive shaft and spring in a central position.
FIG. 10 is a perspective view of a spring mechanism with a workpiece connected thereto, with the drive shaft and spring in a left-rotated position.
FIG. 12 is a perspective view of a spring mechanism with a workpiece connected thereto, with the drive shaft and spring in a right-rotated position.
Figure 9:
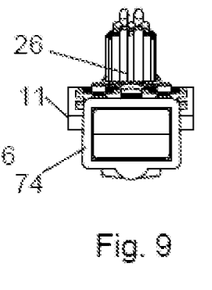
FIG. 9 is a rear view thereof.
Figure 11:
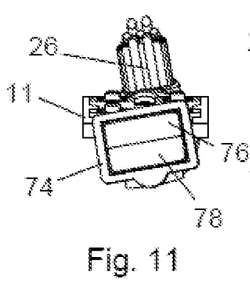
FIG. 11 is a rear view thereof.
Figure 13:
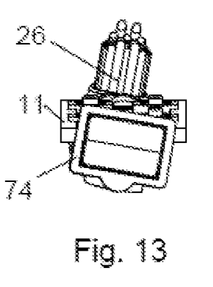
FIG. 13 is a rear view thereof.
Figure 14:
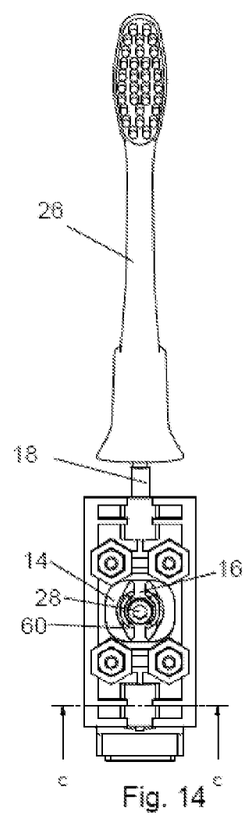
FIG. 14 is a front view of a spring mechanism with a workpiece connected thereto, with the drive shaft and spring in a central position.

The adjustable tuning element 28 connects the drive shaft 18 to the spring 14. More particularly, the adjustable tuning element 28 connects the drive shaft 18 to the movable portion 16 of the spring 14. In the illustrated embodiment, the adjustable tuning element 28 is a threaded bolt that extends through the central opening 66 in the movable section 16 of the spring 14, through the fastener hole 82 in the drive shaft 18, and into a tuning nut 84 on the rear surface of the drive shaft 18. When the bolt 28 is inserted into the nut 84, the drive shaft 18 is connected to the spring 14 and to the fixed element 11 with the engagement surfaces 52 and 80 in engagement with one another to form bearings for the rocking movement of the drive shaft 18. As a result of the threads on the bolt 28, the bolt 28 and nut 84 can be tightened or loosened to adjust the amount of tension placed on the movable section 16 of the spring 14. For example, FIG. 6 shows the tuning element 28 connected to the nut 84 with the movable section 16 of the spring in a generally neutral position aligned with the remainder of the flat spring 14. In this state, there may be a gap between the movable section 16 of the spring 14 and the drive shaft 18. FIG. 7 shows the tuning element 28 connected more tightly onto the nut 84 with the movable section 16 of the spring 14 in a tensioned position wherein the movable section is flexed slightly toward the drive shaft 18, which may partially or completely close the gap between the drive shaft 18 and the spring 14. Variations in the amount of tension on the movable section 16 of the spring 14 will alter the amplitude and frequency of the movement of the drive shaft 18 and the workpiece 26. As such, the manufacturer can efficiently tune the movement of the workpiece 26 by rotating the bolt 28 with respect to the nut 84, therefore drawing the movable section 16 toward the drive shaft 18 and adjusting the tension on the movable section 16 of the spring 14. Alternate fasteners or devices that provide a degree of adjustment may be substituted for the bolt style fastener in variations on the current design.

Notably, although the above disclosed embodiments are shown in connection with toothbrush heads, they may also be used in connection with other types of workpieces that utilize the same or similar ranges of motion, such a cleaning brush and/or an exfoliating brush with bristles arranged generally parallel to the longitudinal length of the drive shaft 18.

III. Operation

During operation, the electromagnet 30 within the drive unit housing 12 is operated by the user manipulating switch 31. When actuated, the electromagnet 30 may oscillate and/or be controlled to change polarities over a range of drive frequencies. The replacement head or other workpiece 26 is connected to the end 24 of the drive shaft 18 by inserting the second end 24 of the drive shaft 18 into the receptacle on the workpiece 26—or by another attachment method. The electromagnet 30, and its attraction to the permanent magnets 76, 78 (or ferromagnetic material) on the base 72 causes the base 72 to oscillate back and forth in an arcuate path.

The spring mechanism 10 controls the path of movement of the drive shaft 18, as well as the amplitude and frequency of movement of the workpiece 26. Referring to spring mechanism 10, the movement of the base 72 causes the drive shaft 18 to rotate back and forth about a rotation axis extending through the bearing surface 80—specifically the engagement surface between the bearing surface 80 and the surfaces 52, 52' of the fixed housing 11 because of the connection between the drive shaft 18 and the movable portion 16 of the spring 14. The rotation axis is general parallel to the spring axis and the longitudinal axis 68 of the drive shaft 18. The movable section 16 of the spring 14 rotates about the spring axis as the drive shaft 18 oscillates, and acts to control the movement of the drive shaft 18 and bias the drive shaft 18 in a central position. As the spring 74 twists, the workpiece 26 moves in an arcuate path.

Figure 17:
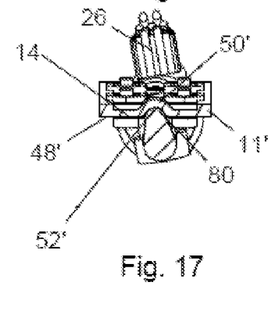
FIG. 17 is a cross sectional view thereof taken along line B-B in FIG. 16.
Figure 18:
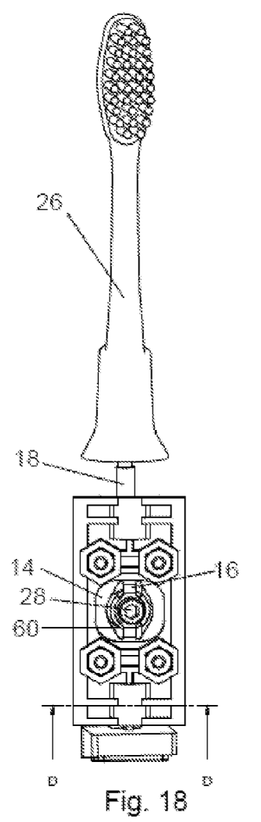
FIG. 18 is a front view of a spring mechanism with a workpiece connected thereto, with the drive shaft and spring in a right-rotated position.
Figure 19:
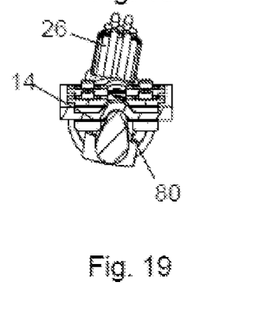
FIG. 19 is a cross sectional view thereof taken along line D-D in FIG. 18.

The motion of the spring mechanism 10 and workpiece 26 is depicted in detail in FIGS. 8-19. FIGS. 8-9 and 14-15 show the spring mechanism 10 in a central position, which may be a neutral resting position when the electromagnet is off, and may be a central position of rotation when the electromagnet is actuated. In this position, the movable portion 16 of the spring 14 lies generally in the same plane as the remainder of the spring 14 in a non-twisted state. As shown in FIG. 15, the bearing surface 80 on the drive shaft engages the surface 52' of the fixed housing 11 (extending through an opening defined in the spring 14) and the bristles 44 on the workpiece 26 are generally perpendicular to the upper surface 46 of the fixed element 11. FIGS. 10-11 and 16-17 show the spring mechanism 10 in a left-rotated position, occurring when the electromagnet is actuated. In this position, the movable portion 16 of the spring 14 lies generally in a plane that is angled with respect to the remainder of the spring 14 in a twisted state. As shown in FIG. 17, the bearing surface 80 on the drive shaft engages the surface 52' of the fixed housing 11 (extending through an opening defined in the spring 14) and the bristles 44 on the workpiece 26 are generally rotated to the left with respect to the upper surface 46 of the fixed element 11. Finally, FIGS. 12-13 and 18-19 show the spring mechanism 10 in a right-rotated position, occurring when the electromagnet is actuated. In this position, the movable portion 16 of the spring 14 lies generally in a plane that is angled to the right with respect to the remainder of the spring 14 in a twisted state. As shown in FIG. 19, the bearing surface 80 on the drive shaft engages the surface 52' of the fixed housing 11 (extending through an opening defined in the spring 14) and the bristles 44 on the workpiece 26 are generally rotated to the right with respect to the upper surface 46 of the fixed element 11. For the duration that the electromagnet 30 is actuated, the spring mechanism 10 oscillates back and forth between the left-rotated and right-rotated positions.

As noted above, the motion and frequency of the workpiece, such as the bristle head 40 or the workpiece of another type of device, may be controlled by a variety of variables. In the present invention, this may include adjustment of the adjustable tuning element 28. Other variables include, but are not limited to, the size, thickness and shape of the spring, the positioning of the magnets on the bottom member, the size and length of the bristles, and the drive frequency of the motor. Each of these variables can be adjusted from application to application to provide a desirable user experience in terms of brushing function, handle vibration and operating noise. In one embodiment, the drive frequency of the motor is between about 60 Hz and 1000 Hz. In a more particular embodiment for use with an electric toothbrush, the drive frequency is between about 150 Hz and 400 Hz. In a more particular embodiment for an electric toothbrush, the drive frequency of the motor is between about 230 Hz and 280 Hz, and in an even more particular embodiment for an electric toothbrush the drive frequency of the motor is set to about 260 Hz. In an embodiment wherein the workpiece is the head of an exfoliator, the drive frequency may be between about 150 and 200 Hz. The drive frequency for alternative workpiece applications, such as those listed above, may be increased or decreased depending on the desired power and workpiece motion for the particular application.

After a particular drive frequency is determined, the above noted variables are adjusted to achieve the desired motion and frequency of the bristle head 40 while maintaining a relatively low sound level and a relatively low current draw on the motor. In one embodiment for use with an electric toothbrush, the desired frequency of the bristle head is between about 245 Hz and 255 Hz. In another embodiment, the desired range of motion of the tips of the bristles is between about 0.370 mm and 0.575 mm. In yet another embodiment, the desired sound level of the operating toothbrush containing one of the above noted embodiments is below about 73 dB, and more particularly, below about 60 dB. If, after assembly and after an initial testing operation, the workpiece movement is found to be incorrect, a manufacturer may simply adjust the tuning element 28 to achieve the desired motion.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A spring mechanism for a power device, the device including an electromagnet, the spring mechanism comprising:
   a housing;
   a spring connected to the housing, wherein at least a portion of said spring is movable with respect to said housing;
   a drive shaft that includes a first end having a magnet and a second end for attachment to a workpiece; and
   an adjustable tuning element connecting said drive shaft to said movable portion of said spring,
   wherein said drive shaft is rotatable about a pair of bearing surfaces defining an axis of rotation extending along said bearing surfaces, and the adjustable tuning element is positioned between said bearing surfaces.

2. The spring mechanism of claim 1 wherein said spring is a flat spring, and said movable portion of said spring is a spring section positioned between a pair of cutouts defined in said spring.

3. The spring mechanism of claim 2 wherein said adjustable tuning element extends from said drive shaft to said movable portion of said spring, said adjustable tuning element connected to said spring such that said adjustable tuning element places said movable portion of said spring under a degree of tension.

4. The spring mechanism of claim 3 wherein said adjustable tuning element is threadedly connected between said drive shaft and said movable portion of said spring, said threaded connection enabling adjustment of the amount of said tension on said movable portion of said spring.

5. The spring mechanism of claim 4 wherein said adjustable tuning element extends generally perpendicular to said axis of rotation.

6. The spring mechanism of claim 5 wherein said adjustable tuning element includes a bolt extending through said movable portion of said spring, through said drive shaft, and into a nut on an opposite surface of said drive shaft.

7. The spring mechanism of claim 6 wherein said bearing surfaces are formed by a pair of rockers extending from said drive shaft.

8. A spring mechanism for a power device, the device including an electromagnet, the spring mechanism comprising:
   an elongated drive shaft having a first end and a second end opposite said first end for attaching to a workpiece, said drive shaft defining a longitudinal axis, said first end including a base extending outwardly from said longitudinal axis, said base including a magnet proximate the electromagnet, the drive shaft is rotatable about an axis of rotation extending parallel to the longitudinal axis;
   a fixed housing including a spring member, said spring member having a movable section capable of torsional rotation about a spring axis, said spring axis generally parallel to said longitudinal axis of said drive shaft, said movable section positioned between said first end and said second end of said drive shaft;
   a tuning member extending between said drive shaft and said movable section of said spring member; and
   at least one bearing surface engagement between said drive shaft and said fixed housing about which said drive shaft can rotate with respect to said fixed housing, wherein said drive shaft is driven to rotationally oscillate upon actuation of the electromagnet.

9. The spring mechanism of claim 8 wherein said spring member is a flat spring and said movable section is defined between a pair of cutouts in said spring member, such that said movable section is surrounded within said spring.

10. The spring mechanism of claim 8 wherein said tuning member is adjustable to adjust a degree of tension on said movable section of said spring in a direction generally perpendicular to said spring axis.

11. The spring mechanism of claim 10 wherein said tuning member is a threaded member extending through said movable section of said spring and through said drive shaft.

12. The spring mechanism of claim 8 wherein at least one bearing surface includes a pair of engagement points between said drive shaft and said fixed housing on opposite sides of said tuning member.

13. The spring mechanism of claim 12 wherein said engagement points each include a rounded protrusion extending from said drive shaft into engagement with said fixed housing.

14. The spring mechanism of claim 13 wherein said spring member includes a pair of bearing cutouts, each said bearing cutout receiving one of said rounded protrusions extending therethrough.

15. The spring mechanism of claim 8 wherein said base at said first end of said drive shaft extends towards said spring member.

16. A method of manufacturing a spring mechanism for an electric toothbrush, comprising:
   providing a fixed housing defining a generally hollow interior;
   providing a drive shaft extending at least in part into the hollow interior of the fixed housing, the drive shaft having a first end and a second end, the first end including a magnet and the second end adapted to receive a workpiece, the drive shaft is rotatable about an axis of rotation extending parallel to the drive shaft;

connecting a spring member to the fixed housing, the spring member having a movable section positioned between said first end and said second end of said drive shaft;

connecting the spring member to the drive shaft with an adjustable tuning member; and adjusting the tuning member to provide a desired degree of tension on the movable section of the spring.

17. The method of claim 16 wherein the adjusting of the tuning member includes drawing the movable section of the spring member towards the drive shaft.

18. The method of claim 17 wherein the spring is a flat spring and the movable section of the spring is positioned between a pair of cutouts defined in the flat spring, such that said movable section is surrounded within said spring.

* * * * *